United States Patent
Morré

(10) Patent No.: US 9,283,257 B2
(45) Date of Patent: Mar. 15, 2016

(54) COMPOSITIONS COMPRISING SOLANUM TUBEROSUM FOR LOWERING CYTOSOLIC NADH LEVEL TO MIMIC CALORIE RESTRICTION

(75) Inventor: D. James Morré, West Lafayette, IN (US)

(73) Assignee: Nox Technologies, Inc., West Lafayette, IN (US)

( * ) Notice: Subject to any disclaimer, the term of this patent is extended or adjusted under 35 U.S.C. 154(b) by 321 days.

(21) Appl. No.: 12/945,520

(22) Filed: Nov. 12, 2010

(65) Prior Publication Data

US 2011/0111069 A1 May 12, 2011

Related U.S. Application Data

(60) Provisional application No. 61/260,655, filed on Nov. 12, 2009.

(51) Int. Cl.
| | |
|---|---|
| *A61K 36/81* | (2006.01) |
| *A61K 36/39* | (2006.01) |
| *A61K 36/48* | (2006.01) |
| *A61K 36/73* | (2006.01) |

(Continued)

(52) U.S. Cl.
CPC .................. *A61K 36/81* (2013.01); *A61K 36/39* (2013.01); *A61K 36/48* (2013.01); *A61K 36/73* (2013.01); *A61K 36/9066* (2013.01); *G01N 33/5735* (2013.01); *G01N 2500/02* (2013.01); *G01N 2500/10* (2013.01)

(58) Field of Classification Search
CPC ... A61K 36/81; A61K 36/00; A61K 36/9066; A61K 36/39; A61K 36/48; A61K 36/73
See application file for complete search history.

(56) References Cited

U.S. PATENT DOCUMENTS

| 6,406,853 B1 | 6/2002 | Spindler | |
|---|---|---|---|
| 6,974,841 B1 * | 12/2005 | Rapisarda | ..................... 514/783 |
| 2004/0028751 A1 * | 2/2004 | Mae et al. | ..................... 424/684 |

(Continued)

FOREIGN PATENT DOCUMENTS

WO 2006/041624 4/2006

OTHER PUBLICATIONS

MacDonald Wayfaring in the Cotswolds; The New York Times; Mar. 9, 1986; A. 16.*

(Continued)

*Primary Examiner* — Patricia A Leith
(74) *Attorney, Agent, or Firm* — Dorsey & Whitney LLP (57) ABSTRACT

Embodiments herein relate to agents that mimic calorie restriction (CR) to extend life span, especially agents that lower the level of cytosolic NADH and increase the level of cytosolic NAD+ (relative to NADH) required to mimic calorie restriction that results in life span extension, at least in part by inhibition by NADH of SIR2, which is a key regulator of life span in both yeast and animals. NADH is a competitive inhibitor of SIR2, an NAD-requiring NAD-dependent histone deacetylase required for chromatin silencing and life-span extension. An overall reduction in NADH activates SIR2 and extends life span. The use of fluorescence measurements of NADH levels in a 96-well plate assay utilizing Baker's yeast (*Saccharomyces cerevisiae*) as a model to screen for agents and supplements that lower NADH levels is disclosed herein. A caloric restriction mimetic contains 1 part Mg2+ malate, 1 part turmeric and 98 parts dehydrated potato skins.

16 Claims, 5 Drawing Sheets (51) Int. Cl.
   A61K 36/9066    (2006.01)
   G01N 33/573    (2006.01)

(56) References Cited

U.S. PATENT DOCUMENTS

| | | | |
|---|---|---|---|
| 2006/0189512 | A1 | 8/2006 | Ehrenkranz |
| 2007/0077310 | A1 | 4/2007 | Zemel et al. |
| 2008/0032033 | A1* | 2/2008 | Nie et al. .................. 426/656 |
| 2008/0279786 | A1 | 11/2008 | Cash |
| 2008/0293777 | A1 | 11/2008 | Erlanson et al. |
| 2009/0252796 | A1 | 10/2009 | Mazed et al. |
| 2010/0048545 | A1 | 2/2010 | Jette et al. |
| 2010/0081681 | A1 | 4/2010 | Blagosklonny |
| 2010/0087527 | A1 | 4/2010 | DiMauro |

OTHER PUBLICATIONS

Maxmen, A. Calorie Restriction Falters in the Long Run; Nature News; Aug. 29, 2012, pp. 1-7.*
eHOW.com eHOW.com: How to Use Turmeric in Recipes; URLhttp://www.ehow.com/how_5650816_use-turmeric-recipes. html accessed Apr. 26, 2013.*
Singh et al. Protective Effect of Potato Peel Powder in Ameliorating Oxidative Stress in Streptozotocin Diabetic Rats; Plant Foods for Human Nutrition 60; 49-54 (2005).*
Hwang et al. (2009) "Pharmacological Stimulation of NADH Oxidation Ameliorates Obesity and Related Phenotypes in Mice," Diabetes 58:965-974. (Published on the web Jan. 2009).
Ingram et al. (2004) "Development of Calorie Restriction Mimetics as a Prolongevity Strategy," Ann NY Acad Sci 1019:412-423.
Kyriazis, M. (printed Oct. 20, 2010) "Calorie Restriction Mimetics," http://www.antiaging-systems.com/ARTICLE-496/calorie-restriction.htm, 5 pages.
Reinicke et al. (2005) "Development of β-Lapachone Prodrugs for Therapy Against Human Cancer Cells with Elevated NAD(P)H:Quinone Oxidoreductase 1 Levels," Clin Cancer Res 11(8):3055-3064.
Rodriguez et al. (2008) "Improved Mitochondrial Function and Increased Life Span After Chronic Melatonin Treatment in Senescent Prone Mice," Exp Gerontol 43(8):749-756. (Abstract only).
Roth et al. (2001) "Caloric Restriction in Primates and Relevance to Humans," Ann NY Acad Sci 928:305-315.
Smith et al. (2010) "Calorie Restriction: What Recent Results Suggest for the Future of Ageing Research," Eur J Clin Invest 40(5):440-450.
Search Report and Written Opinion, dated Mar. 14, 2011, for International Application No. PCT/US10/56595, filed Nov. 12, 2010, a corresponding application, 9 pp.
Andre et al. (2007) "Antioxidant Profiling of Native Andean Potato Tubers (Solanum tuberosum L.) Reveals Cultivars with High Levels of β-Carotene, α-Tocopherol, Chlorogenic Acid, and Petanin," J. Agric. Food Chem. 55(26):10839-10849.
Baur et al. (2006) "Resveratrol improves health and survival of mice on a high-calorie diet," Nature 444:337-342.
Berge et al. (1977) "Pharmaceutical Salts," J. Pharmaceutical Sciences 66:1-19.
Bishop et al. (2007) "Genetic links between diet and lifespan: shared mechanisms from yeast to humans," Nature Reviews: Genetics 8:835-844.
Bordone et al. (Apr. 2005) "Calorie Restriction, SIRT1 and Metabolism: Understanding Longevity," Nature Reviews: Mol. Cell Biol. 6:298-305.
Campos et al. (2006) "Antioxidant capacity and secondary metabolites in four species of Andean tuber crops: native potato (Solanum sp.), mashua (Tropaeolum tuberosum Ruiz & Pavón), Oca (Oxalis tuberosa Molina) and ulluco (Ullucus tuberosus Caldas)," J. Sci. Food Agric. 86:1481-1488.
Cash, A. (only publication dated Sep. 30, 2009) "Oxaloacetic Acid Supplementation as a Mimic of Calorie Restriction," Open Longevity Science 3:22-27.
Cevallos-Casals et al. (2003) "Stoichiometric and Kinetic Studies of Phenolic Antioxidants from Andean Purple Corn and Red-Fleshed Sweetpotato," J. Agric. Food Chem. 51:3313-3319.
Cohen et al. (2004) "Calorie Restriction Promotes Mammalian Cell Survival by Inducing the SIRT1 Deacetylase," Science 305:390-392.
Dhahbi et al. (2005) "Identification of potential caloric restriction mimetics by microarray profiling," Physiol Genomics 23:343-350.
Dukes et al. (1994) "Dependence on NADH Produced during Glycolysis for β-cell Glucose Signaling," J. Biol. Chem. 269(15):10979-10982.
Easlon et al. (Apr. 2008) "The malate-aspartate NADH shuttle components are novel metabolic longevity regulators required for calorie restriction-mediated life span extension in yeast," Genes & Development 22:931-944.
Ejaz, et al. (posted May 19, 2009) "Turmeric extract suppresses fat tissue growth in rodent models," (Internet Review of: Kim, et al. (2009) "Dietary Curcumin and Limonin Suppress $CD4^+$ T-Cell Proliferation and Interleukin-2 Production in Mice$^{1-3}$," Journal of Nutrition 139(5):1042-1048.).
Giannakou et al. (2004) "The interaction between FOXO and SIRT1: tipping the balance towards survival," Trends in Cell Biol. 14(8):408-412.
Guarente et al. (Feb. 25, 2005) "Calorie Restriction—the SIR2 Connection," Cell 120:473-482.
Guarente (Jan. 25, 2008) "Mitochondria—A Nexus for Aging, Calorie Restriction, and Sirtuins?," Cell 132:171-176.
Haigis et al. (2006) "Mammalian sirtuins—emerging roles in physiology, aging, and calorie restriction," Genes Dev. 20:2913-2921.
Hale, A. L. (Dec. 2003) Dissertation entitled "Screening Potato Genotypes for Antioxidant Activity, Identification of the Responsible Compounds, and Differentiating Russet Norkotah Strains Using AFLP and Microsatellite Marker Analysis" Texas A&M University, 260 pp.
Holt, S. (Oct. 1, 2009) "Natural therapeutics: calorie restriction mimetics," Townsend Letter, 7 pages.
Howitz et al. (2003) "Small molecule activators of sirtuins extend Saccharomyces cerevisiae lifespan," Nature 425:191-196.
Ingram et al. (2006) "Calorie restriction mimetics: an emerging research field," Aging Cell 5:97-108.
Kaeberlein et al. (1999) "The SIR2/3/4 complex and SIR2 alone promote longevity in Saccharomyces cerevisiae by two different mechanisms," Genes & Dev. 13:2570-2580.
Kim, et al. (online publication Mar. 25, 2009) "Dietary Curcumin and Limonin Suppress $CD4^+$ T-Cell Proliferation and Interleukin-2 Production in Mice$^{1-3}$", Journal of Nutrition 139(5):1042-1048.
Kyriazis, M. (2009) "Calorie Restriction Mimetics: Examples and Mode of Action," Open Longevity Science 3:17-21. (date of publication unknown).
Lin et al. (2002) "Calorie restriction extends Saccharomyces cerevisiae lifespan by increasing respiration," Nature 418:344-348.
Lin et al. (2004) "Calorie restriction extends yeast life span by lowering the level of NADH," Genes & Development 18:12-16.
Methuselah Foundation Newsletter, "The Spice of Life: Is Curcumin the Answer for Longevity?," Downloaded from the internet on Oct. 26, 2010, 1 page (no author given). http://methuselahfoundation.org/new_newsletter/septnl_mid.html.
Michalow, A. E. (Apr. 2008) "Enhancing Longevity: Novel Caloric Restriction Mimetics," Rejuvenation Research 11(2):473-477.
Nisoli et al. (2005) "Calorie Restriction Promotes Mitochondrial Biogenesis by Inducing the Expression of eNOS,"Science 310:314-317.
Panowski et al. (2007) "PHA-4/Foxa mediates diet-restriction-induced longevity of C. elegans," Nature 447:550-556.
Rabah et al. (2005) "Increase in Antioxidant and Cytotoxicity Through Apoptosis-induction on HL-60 of Sweet Potato (Ipomoea Batatas Lam. cv. Koganesengan) by Sub-critical Water Treatment," Food Sci. Technol. Res. 11(1):122-126.
Roth et al. (2001) "Dietary Caloric Restriction Prevents the Age-Related Decline in Plasma Melatonin Levels of Rhesus Monkeys," J. Clin. Endocrinol. Metab. 86(7):3292-3295.
Schulz et al. (2007) "Glucose Restriction Extends Caenorhabditis elegans Life Span by Inducing Mitochondrial Respiration and Increasing Oxidative Stress," Cell Metabolism 6:280-293.

(56) References Cited

OTHER PUBLICATIONS

Thompson et al. (online publication Sep. 26, 2008) "Functional food characteristics of potato cultivars (*Solanum tuberosum* L.): Phytochemical composition and inhibition of 1-methyl-1-nitrosourea induced breast cancer in rats," Journal of Food Composition and Analysis 22:571-576.

Walford et al. (1987) "Dietary Restriction and Aging: Historical Phases, Mechanisms and Current Directions," J. Nutrition 117:1650-1654.

Weindruch et al. (1988) "Influences of Aging and Dietary Restriction on Serum Thymosin$_{\alpha 1}$ Levels in Mice," J. Gerentol. 43:B40-B42.

Yu, Masoro and McMahan (1985) "Nutritional Influences on Aging of Fischer 344 Rats: I. Physical, Metabolic, and Longevity Characteristics," J. Gerentol. 40(6):657-670.

Zhao et al. (Jan. 2009) "Pharmacological and nutritional activities of potato anthocyanins," African Journal of Pharmacy and Pharmacology 2(10):463-468.

\* cited by examiner

COMPOSITIONS COMPRISING SOLANUM TUBEROSUM FOR LOWERING CYTOSOLIC NADH LEVEL TO MIMIC CALORIE RESTRICTION

BACKGROUND

The field of this invention is the modification of metabolism to mimic caloric restricted conditions without the usual reduction in calorie content, specifically, by lowering the overall level of cytosolic reduced pyridine nucleotide (NADH), especially relative to the $NAD^+$ level, by administration of a nutritional supplement composition based on a high throughput assay of suppression of NADH autofluorescence in *Saccharomyces cerevisiae*.

Calorie restriction is the only experimental manipulation known to extend the life span of living organisms (Lin et al., 2002, Nature 418:344-348; Weindruch and Walford, 1998, The Retardation of Aging and Disease by Dietary Restriction, Charles C. Thomas, Springfield, Ill.; Roth et al., 2001, J. Clin. Endocrinol. Metab. 86:3292-3295). A major cause of aging is thought to result from the cumulative effects of cell loss over time (Cohen et al., 2004, Science 305:390-392). The proposed mechanism underlying extension of life span involves a shift from a state of growth and proliferation to maintenance and repair (Walford, Harris and Weindruch, 1987, J. Nutrition 117: 1650-1654; Weindruch et al., 1988, J. Gerentol. 43: 840-842; Yu, Masoro and McMahan, 1985, J. Gerentol. 40: 657-670).

Initially, calorie restriction was believed to extend life span by decreasing metabolic rate, decreasing mitochondrial oxygen consumption, and, therefore, attenuating oxidative stress. However, the exact opposite appears to be true evidenced by increases in mitochondrial content and oxygen consumption in response to calorie restriction (Nisoli et al., 2005, Science 310:314-317). Observations that calorie restriction does not increase life span when the gene encoding cytochrome c is deleted (Lin et al., 2002, Nature 418:344-348) or in the presence of electron transport inhibitors (Bishop and Guarente, 2007, Nutr. Rev. Genet. 8:835-844; Pankowski et al., 2007, Nature 447:550-555) suggest that mitochondria are critical factors in the phenomenon of life span extension by calorie restriction.

There are several mechanisms by which mitochondria may be responsible for the life-enhancing effects of calorie restriction (Guarente, 2008, Cell 132:171-176). However, our work suggests that the simplest and most likely explanation is that enhanced mitochondrial activity results in the depletion of reduced pyridine nucleotides (NADH) of the cytosol and the increased production of $NAD^+$ and that lowering of the level of NADH results in life extension. Among the several determinants of life span, the one common thread that has emerged is a variety of species from yeast to rodents is a correlation with lowered levels of NADH.

The basis for life extension by lowered NADH and increased $NAD^+$ is due in part to inhibition by NADH of SIR2, a key regulator of life span in a number of organisms including yeast, worms, flies, rodents and non-human primates (Bordone and Guarente, 2005, Nat. Rev. Mol. Cell Biol. 6:298-305). That the silent information regulator (Sir) proteins regulate life span is well known (Haigis and Guarante, 2006, Genes Dev. 20:2913-2921). In yeast, an extra copy of the SIR2 gene extends replicative life span by 50 percent, while deleting SIR2 shortens life span (Kaberlein et al., 1999, Genes Dev. 20:2570-2580). SIR2 encodes an NADP-dependent deacetylase which emerges as a critical mediator of calorie restriction (Guarente and Picard, 2005, Cell 120:473-482).

The mammalian SIR2 ortholog SIRT1 encodes an NAD-requiring NAD-dependent histone deacetylase required for chromatin silencing and life-span extension. NADH is a competitive inhibitor of SIR2. Therefore, an overall reduction in NADH will activate SIR2 and result in life extension.

Calorie restriction mimics modify metabolism to reduce NADH levels and increase $NAD^+$ comparable to that achieved under calorie restriction conditions, without the usual reduction in calorie content.

With extended use, calorie restriction mimics up- and down-regulate gene expression and cellular proteins to resemble those associated with calorie-restricted profiles as well as to decrease insulin resistance (lower fasting blood glucose levels) and increase glucose uptake, also similar to changes seen in calorie restriction. The same life extending pathways that have been shown to increase health and life span in animal trials are modified.

Longevity regulatory genes in addition to the NAD dependent histone deacetylase silent information regulator (SIR2) include, as well, the Forkhead transcription factor FOXO (Giannakou and Partridge, 2005, Trends Cell Biol. 14:408-412).

There is a long felt need in the art to provide compositions for human and animal use which extend longevity and which improve function of metabolism, so as to benefit health and wellbeing.

DEFINITIONS

As used herein, the term "calorie restriction (CR)" refers to the dietary manipulations in yeast, worms, flies, rodents and other mammals, including humans, that result in increased life span through reduction of caloric intake in concert with vitamin and antioxidant supplementation.

As used herein, the term "calorie restriction mimic" or "calorie restriction mimetic" is a substance, mixture of substances or nutritional supplement that recapitulate calorie restriction conditions without the usual requirement for a reduction in calorie content of the diet. Advantageously, the $NAD^+$/NADH ratio is increased.

As used herein, the term "glycolytic inhibitor" refers to any substance, mixture of substances or nutritional supplement capable of reducing cytosolic levels of NADH by interfering with glycolytic NADH production.

As used herein, the term "subject" or "individual" means a mammal. In certain embodiments, the mammal is a human while in others, the mammal is a non-human primate. Alternatively, the subject is a domesticated mammal, such as companion animal or pet animal, e.g., canine, feline, murine, etc., or a farm animal, e.g., bovine, equine, ovine, caprine, etc.

As used herein, the terms "a subject in need of weight loss" means a subject that is at least about 10 percent above its ideal weight. In certain embodiments the subject is at risk of further weight gain.

The phrase, "pharmaceutically acceptable derivative", as used herein, denotes any pharmaceutically acceptable salt, ester, or salt of such ester, of such compound, or any other adduct which, upon administration to a patient, is capable of providing (directly or indirectly) a compound as otherwise described herein, or a metabolite or residue thereof. In the case of Krebs cycle acids, the salt is typically the result of complexation or association with a cation, such as divalent magnesium or monovalent sodium ion for example, or other cation which is nontoxic and palatable to the human or animal subject of choice.

The term "treating", as used herein generally means that the compounds disclosed herein can be used in humans or animals in which extended life and improved metabolism and well-being are desired. In certain embodiments, compounds disclosed herein will delay or slow the progression of the disease or condition, thereby giving the subject a longer life span or a better quality of life.

Body mass index ("BMI"), also called the Quetelet number or Quetelet index, is currently the most widely accepted calculation of excess body fat for humans. Developed by Adolphe Quetelet, BMI is calculated by dividing the subject's weight by the square of his/her height (BMI=W/h.sup.2). In SI units, BMI is typically given as kg/m.sup.2; in English units, BMI is typically given as Ib/in$^2$. For example, a person who weighs 75 kilograms and stands 1.8 meters tall would have a BMI of $75/(1.8^2)=23.148$, and thus would not be in need of weight loss. However, a person who weighs 100 kilograms and stands 1.8 meters tall would have a BMI of $100/(1.8)^2=30.864$ and therefore would both be in the "obese" range, and thus in need of weight loss.

A pharmaceutically acceptable derivative includes, but is not limited to, pharmaceutically acceptable salts, esters, salts of such esters, or any other adduct or derivative which upon administration to a subject in need is capable of providing, directly or indirectly, a compound as otherwise described herein, or a metabolite or residue thereof.

SUMMARY

Figure 1:
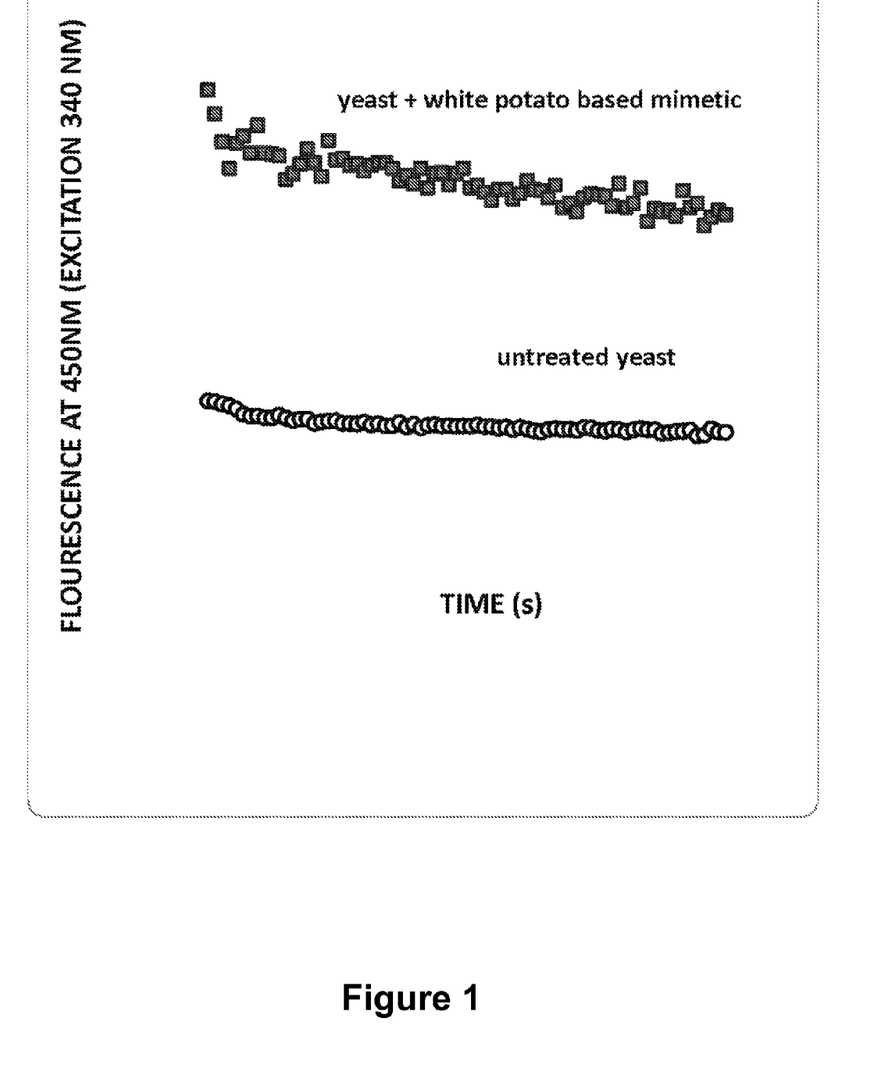
FIG. 1 illustrates NADH depletion as ascertained by NADH auto-fluorescence over time in untreated wild type yeast and in yeast treated with a brown potato-based CR mimetic formulation.
Figure 2:
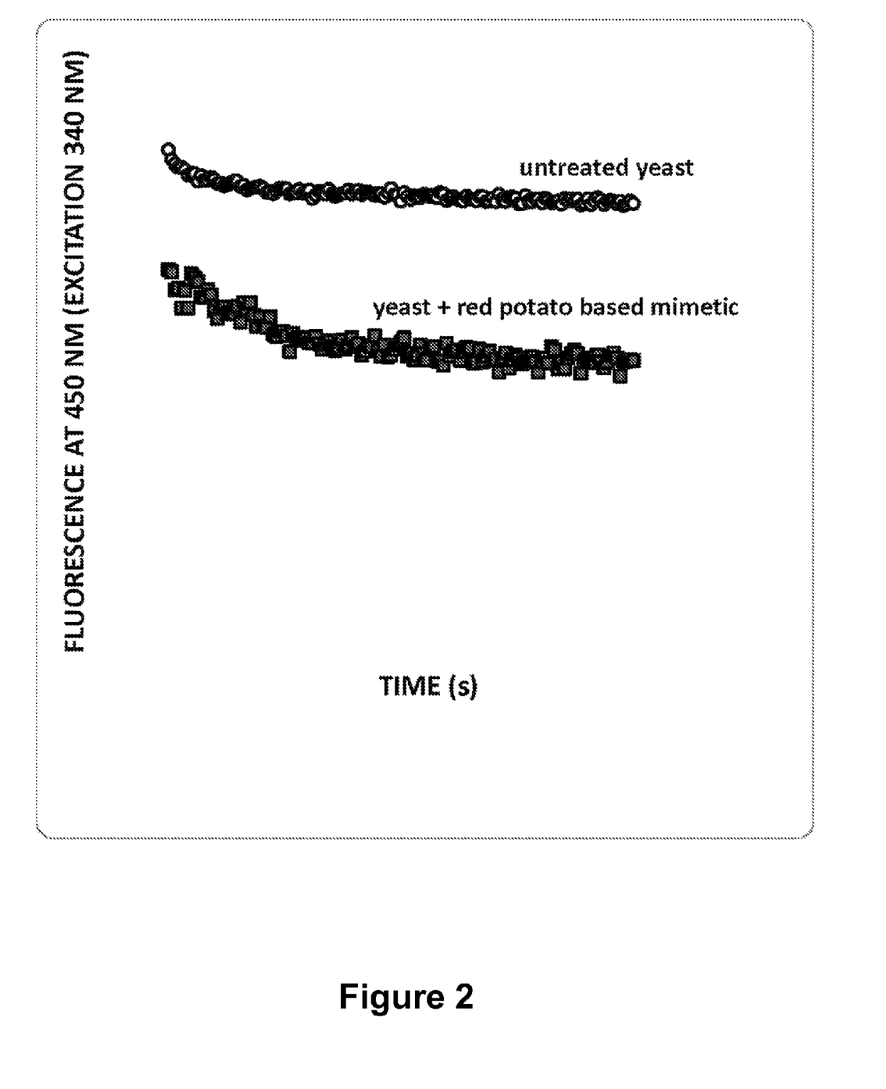
FIG. 2 illustrates NADH depletion as ascertained by NADH auto-fluorescence over time in untreated wild type yeast and in yeast treated with a red potato-based CR mimetic formulation.
Figure 3:
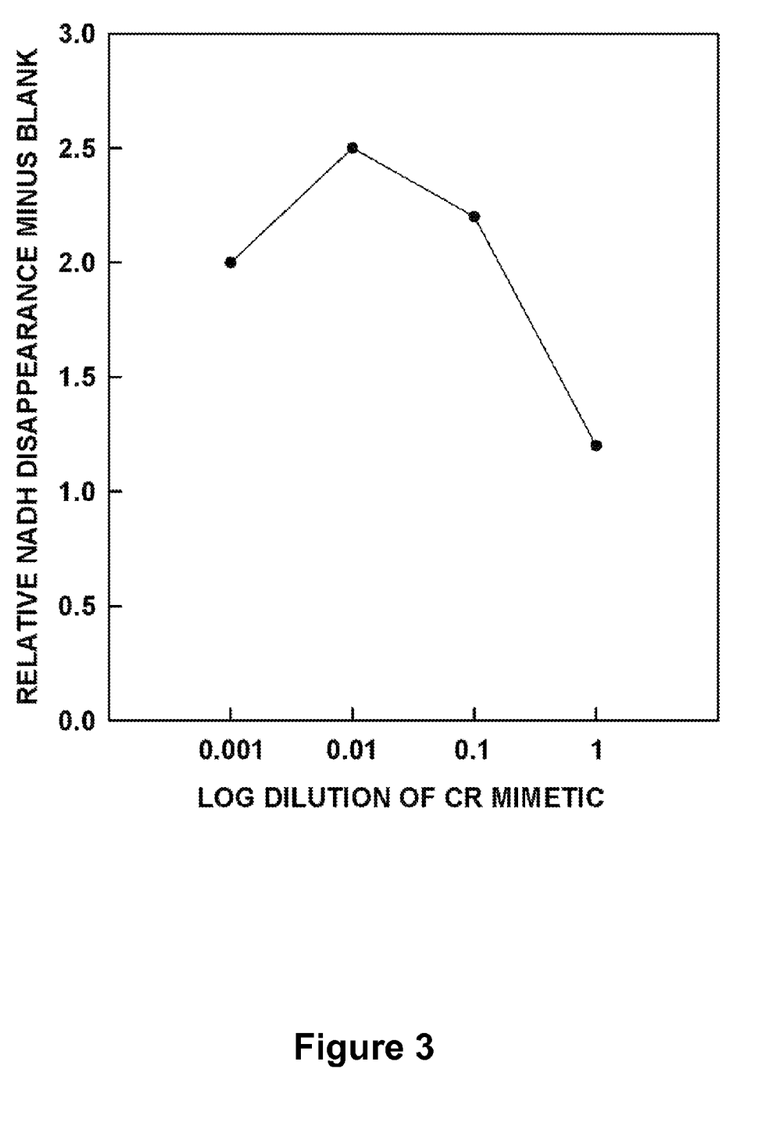
FIG. 3 documents relative NADH disappearance (yeast assay) as a function of dilution of a preferred embodiment of a red potato skin-based CR mimetic formulation.
Figure 4:
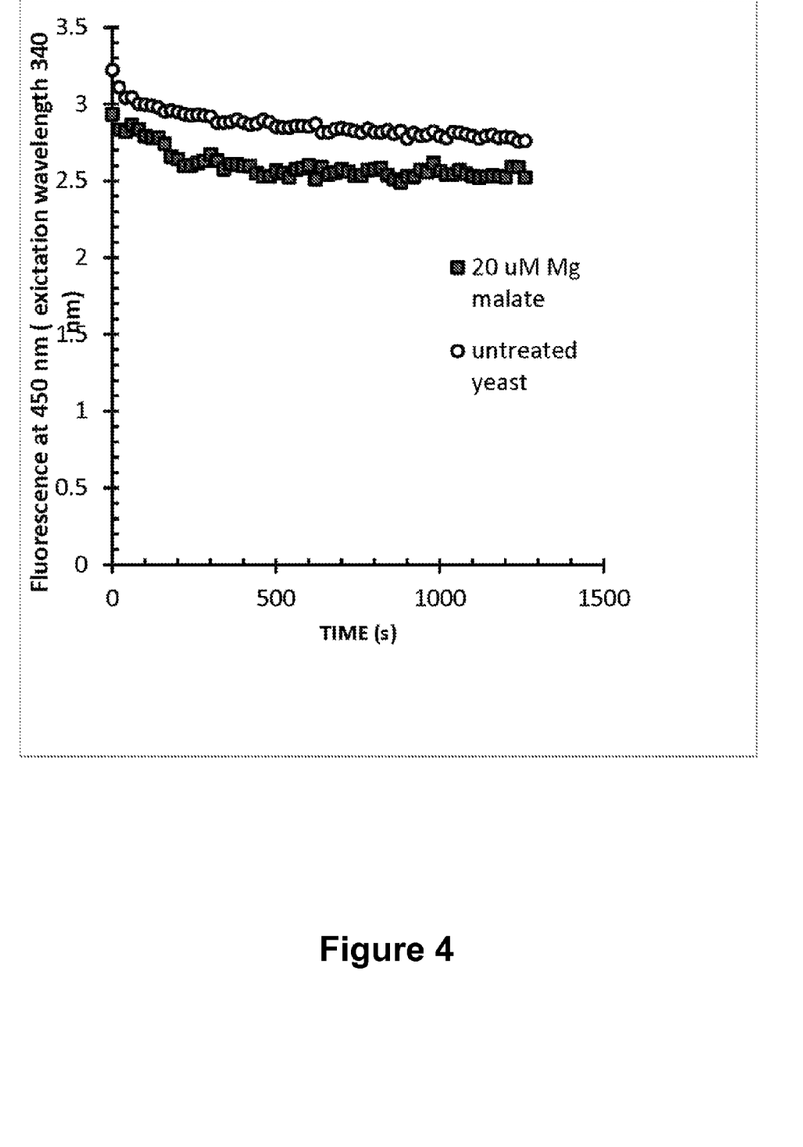
FIG. 4 illustrates NADH depletion as ascertained by NADH auto-fluorescence over time in untreated wild type yeast and in yeast treated with Mg$^+$ malate alone.
Figure 5:
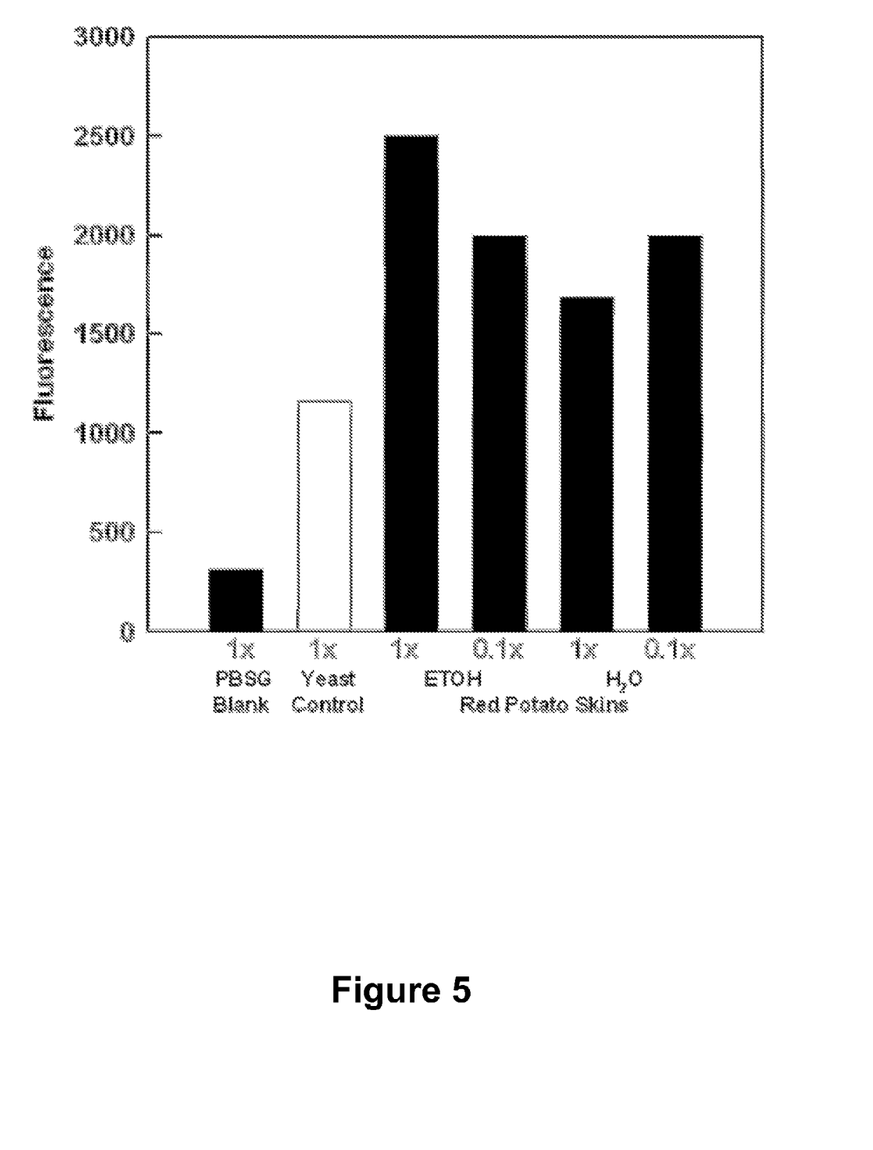
FIG. 5 shows the results for fluorescence measurements of depletion of NADH levels comparing an infusion of freeze-dried red Irish potato skins (125 mg/ml boiling water, cooled to room temperature and steeped overnight) with a tincture (125 mg/ml ethanol) prepared in parallel at two dilutions. The 1× final dilution was 1:20, and the 0.1× dilution was 1:200.

Embodiments and methods as disclosed herein modify metabolism in a mammal with agents that mimic calorie restriction without the usual reduction in calories when administered to a mammal in an amount sufficient for such modification and methods for identification of agents that mimic calorie restriction without the usual reduction in calories.

In certain embodiments modification of metabolism to mimic calorie restriction may be achieved by lowering the overall cytosolic level of reduced pyridine nucleotides (NADH) and a corresponding increase in oxidized pyridine nucleotides (NAD$^+$) by using nutritional supplements, based on a high throughput assay of suppression of NADH autofluorescence in specific strains of Baker's yeast (*Saccharomyces cerevisiae*) to identify compositions with the desired biological activity. Administration of these mostly naturally occurring calorie restriction mimics, alone or in combination, provide a method of intervention to reduce age-related morbidities and extend life span in humans or in animals, especially in companion animals. In one exemplary embodiment, lowering of cytosolic NADH fluorescence in selected yeast strains in response to treatment with a test agent can be used in a method to identify calorie restriction mimics useful in higher organisms. In another exemplary embodiment, unique agents so identified as calorie restriction mimics may be formulated as single agents, mixture of ingredients or as nutritional supplements. Advantageously, the calorie restriction mimetics are combined in a sustained release formulation.

The present methods are based, at least in part, on lowering NADH levels and increasing NAD$^+$ levels, i.e., increasing the NAD$^+$/NADH ratio, in order to relieve the inhibition by NADH of the activity of the enzyme SIR2 as a key regulator of life span in both yeast and mammals. SIR2 is an NAD$^+$-requiring NAD$^+$-dependent histone deacetylase required for chromatin silencing and life span extension. NADH is a competitive inhibitor of SIR2. Therefore, overall reduction of NADH or an increase in the NAD$^+$/NADH ratio activates SIR2 and results in life span extension.

Other embodiments described herein comprise methods (screening assays) to identify agents that mimic calorie restriction by sequestering NADH. In one embodiment, there are methods for reducing cytosolic NADH concentration in the cytosol to mimic calorie restriction and/or increasing the NAD$^+$/NADH ratio.

In another embodiment, the compositions that mimic calorie restriction are provided by various modes of administration, including but not limited to, oral, mucosal and/or topical administration, or also intradermal, transdermal, intravenous or other mode of administration. Oral formulations may be in the form of capsules, tablets, soft gels and solutions or suspensions, nutritional supplement bars or other snack items, for example.

In various other exemplary embodiments, the compositions further include a pharmaceutically acceptable carrier or at least one other biologically active ingredient. In some exemplary embodiments, the mimics may be present with other health aids such as vitamins, minerals and antioxidants and other nutrient compositions from natural sources. In various exemplary embodiments, the calorie restriction mimics from one source are augmented by the effects of calorie restriction mimetics from another source.

Embodiments herein provide compounds and compositions useful for extension of a healthy life comprising at least one agent capable of reducing cytosolic NADH to levels that mimic calorie restriction. A specifically exemplified embodiment consists of 1 part Mg malate, 1 part turmeric and 98 parts finely ground dehydrated potato skins. The potato skins can be from any source of Irish potato (*Solanum tuberosum*) of any variety. Alternatively, compositions comprising sweet potato (*Ipomea batas*) skins or hulls of a pigmented bean (*Phaseolus vulgaris*) can be used, for example, together with malic acid or a pharmaceutically acceptable salt of malic acid, and turmeric, and optionally further comprising oxaloacetic acid or a pharmaceutically acceptable thereof, and optionally in addition to or instead, a preparation comprising sugar-free apple extracts or apple products, including such an apple derived composition in place of malic acid or salt thereof.

Each of the foregoing components may be formulated into compositions that are suitable for administration to a mammal, including a human, including into pharmaceutical compositions containing a therapeutically effective amount of the compound, or into dietary health supplement compositions containing an effective amount of the compound. Each of the foregoing compounds and compositions may be useful in methods of treating obesity, treating overweight or high weight conditions, methods of reducing weight, methods of inducing weight loss, methods of increasing metabolism, up- and down-regulation of gene expression and cellular proteins that recapitulate calorie-restricted profiles as well as to decrease insulin resistance and/or increase glucose uptake.

The $Mg^{2+}$ malate may be replaced by malic acid, other pharmaceutically acceptable salt(s) of malic acid or oxaloacetic acid or a pharmaceutically acceptable salt thereof. Natural sources such as apple (*Malus* spp) for malic acid or *Coleus* (*Coleus* spp) or strawberry (*Frageria* spp) leaves for oxaloacetic acid can be used as well.

Those of skill in the art recognize that the calorie restriction mimics described herein can be administered in any convenient manner. In some embodiments such forms of administration include gel capsules, tablets or sustained release granules. In these and other exemplary embodiments, the calorie restriction mimics are provided at an amount between 200 and 1200 mg/capsule or tablet. A typical dosage for an adult human is about 400 to 1200, or about 500-800, or 600 mg/day, advantageously from 6 to 18 mg per kg body weight. A subject with a body mass of greater than 25 benefits from a higher dose, for example the same dosage administered twice a day rather than once.

In various embodiments presented herein, the magnitude of a therapeutic dose of calorie restriction mimic in the pursuit of a nutritious diet that improves health and extends life span varies with the nature of the mimic and the route of administration. The dose and dose frequency may also vary according to the age, body weight, condition and response of the individual recipient, and the particular mimic combination used. All materials described herein are encompassed as effective calorie restriction mimics and it is understood that one skilled in the art would be able to determine a proper dosage of a particular mimetic mixture using the parameters provided in the invention. In general, the total daily dose ranges of the active materials for the conditions described herein are generally from about 10 mg to about 2000 mg, 200 to 1200, 400 to 800, or 600 mg administered in divided doses administered parenthetically or orally. A preferred total daily dose is from 400 mg to about 1200 mg divided over two equal doses per day, morning and evening.

Dosing can also be determined, taking into account the body mass index of the person taking the supplement described herein. For example, based on a BMI between 18.5 and 24.9, a 600 mg capsule can be administered once per day. For a person with a BMI of over 25, a 600 mg capsule can be administered twice daily (1 morning and 1 evening). This regimen is suggested for the capsule containing 98 parts dried Irish potato skins, 1 part turmeric and 1 part magnesium malate. Similar dosages can be created with these and other materials described herein either singly or in various ratios departing from a specifically exemplified embodiment. For example, curcumin may be substituted for turmeric in the mixture with dried Irish potato skins and 1 part magnesium malate, taking into account that from 0.1 to about 5% (wt/wt) of the turmeric is curcumin.

In another aspect, the present methods are directed to an obesity treatment method comprising administering to an obese subject an effective amount of a composition described herein to induce weight loss in said subject.

The present compositions and methods relate to promoting good physical health and condition and extending longevity in an individual (human or animal) consuming the compositions on a regular basis. A benefit of the regular administration of the compositions described herein is induction of weight loss, especially when coupled with a healthy diet.

The compositions disclosed herein may also be used in combination with dietary therapy, behavioral therapy, physical therapy, exercise, administration of metabolism-stimulating or appetite suppressing compositions, and weight loss surgery, or a combination of two or more such therapies. In some embodiments, the subject is on a calorie restricted diet. In some embodiments, the subject engages in or is to engage in a physical exercise or physical therapy regimen. In some embodiments, the subject has undergone, or will undergo, weight loss surgery.

The methods and compositions described herein may be used to treat humans having a BMI above the recommended body mass index, i.e., at least in the "overweight" range, or at least in the "obese" range. In one embodiment, a human subject is considered in need of weight loss when his or her BMI is 25 or above. In other embodiments, the methods may be used for the purpose of treating humans having a body mass index of at least about 25, above 25, at least about 30, or above 30. Prolonged longevity and improved benefits to appearance and general wellbeing result.

Administration of the compositions described herein are useful when administered to a subject who has not been diagnosed as having a disease or condition at the time of administration, but who would normally be expected to develop the disease or condition or be at increased risk for the disease or condition, especially an aging condition or metabolic disease. The compositions disclosed herein slow the development of disease symptoms, ameliorate disease symptoms, delay the onset of disease, or prevent the subject from developing the disease at all. Preventing also includes administration of the compounds disclosed herein to those subjects thought to be predisposed to the disease due to familial history, genetic or chromosomal abnormalities, and/or due to the presence of one or more biological markers for the disease. In the present context, preventing is not meant to be absolute, but rather an improvement over the natural course of decline in the absence of the administration of the present compositions in an amount effective to increase the $NAD^+/NADH$ ratio. Administration of these compositions also prolongs life in the subjects to which they are regularly administered, with beneficial effects on general health and wellbeing of those subjects.

In another aspect, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents or they may be administered to subjects being treated with other therapeutic and/or biologically active compositions.

It will also be appreciated that certain of the compounds disclosed herein can exist in free form for treatment, or where appropriate, as a pharmaceutically acceptable derivative thereof.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound disclosed herein that, upon administration to a recipient, is capable of providing, either directly or indirectly, a compound as otherwise described herein, or a metabolite or residue thereof.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds disclosed herein include those derived from suitable inorganic and organic acids and bases. Salts derived from appropriate bases include alkali metal, alkaline earth metal, ammonium, and $N+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As described above, the pharmaceutically acceptable compositions disclosed herein may additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds disclosed herein, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; cyclodextrin-type compounds such as Captisol (anionically charged sulfobutyl ether β-cyclodextrin, trademark, CyDex Pharmaceuticals, Inc., Lenexa, Kans.); Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

According to the present invention, the compounds and compositions disclosed herein may be assayed in any of the available assays known in the art. For example, the assay may be cellular or non-cellular, in vivo or in vitro, high- or low-throughput format, etc. Advantageously, the autofluorescence assay described herein is used to identify those compounds and compositions which reduce NADH and/or increase the $NAD^+$/NADH ratio.

In yet another aspect, compositions and methods for the treatment or lessening the severity of overweight or obesity and diseases or conditions associated therewith or the physical effects of aging and for prolonging longevity are provided, comprising administering an effective amount of the composition to a subject in need thereof. In certain embodiments an "effective amount" of the composition is that amount effective for treating or lessening the severity of physical decline associated with aging or overweight or obesity and diseases or conditions associated therewith. The compositions may be administered using any amount and any route of administration effective for treating or lessening the severity of overweight or obesity and diseases or conditions associated therewith, although oral administration is advantageous. The exact amount required may vary from subject to subject, depending on the species, age, weight or BMI and general condition of the subject, the particular composition, its mode of administration, and the like. The compositions disclosed herein are preferably formulated in dosage unit form for ease of administration and uniformity of dosage. The expression "dosage unit form" as used herein refers to a physically discrete unit of agent appropriate for the subject, e.g., a human patient, to whom it is administered. It is understood, however, that the total daily usage of the compositions disclosed herein is advantageously decided by the attending physician within the scope of sound medical judgment with respect to the human patient. The specific effective dose level for any particular human patient or other subject depends upon a variety of factors including the disorder being treated and the severity of the disorder; the activity of the specific compound employed; the specific composition employed; the age, body weight, body mass index, general health and diet of the subject; the time of administration, route of administration, and rate of excretion of the specific compound employed; the duration of the treatment; drugs used in combination or coincidental with the specific compound employed, and like factors well known in the medical or veterinary arts.

Solid dosage forms include tablets, pills, capsules or snack items into which the dose of the composition described herein can be incorporated for ingestion. Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

In order to prolong the effect of a composition disclosed herein, it is often desirable prepare it as a sustained release composition, as known to the art. This may be accomplished by the use of a liquid suspension of crystalline or amorphous material with poor water solubility. The rate of absorption of a compound then depends upon its rate of dissolution that, in turn, may depend upon crystal size and crystalline form.

Compositions for rectal or vaginal administration are preferably suppositories which can be prepared by mixing the compounds disclosed herein with suitable non-irritating excipients or carriers such as cocoa butter, polyethylene glycol or a suppository wax which are solid at ambient temperature but liquid at body temperature and therefore melt in the rectum or vaginal cavity and release the active compound. Where such a mode of administration is to be accomplished, it is preferred that the materials from dried potato skins (or other similar plant matter) are in the form of dehydrated material from an infusion or a tincture) and incorporated into the composition.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like. However, metabolizable carbohydrate materials are not the most preferred.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound disclosed herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. Where such a mode of administration is to be accomplished, it is preferred that the materials from dried potato skins (or other similar plant matter) are in the form of dehydrated material from an infusion or a tincture) and incorporated into the composition.

It will also be appreciated that the pharmaceutically acceptable compositions disclosed herein can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a compound may be administered concurrently with another agent used to treat the same disorder), or they may achieve different effects (e.g., control of any adverse effects). As used herein, additional therapeutic agents that are normally administered to treat or prevent a particular disease or condition are known as "appropriate for the disease, or condition, being treated".

In general, any of the methods disclosed herein may further employ administration to the subject of one or more additional therapeutic agents. Additional therapeutic agents may be selected from among appetite suppressants, neurotransmitter reuptake inhibitors, dopaminergic agonists, serotonergic agonists, modulators of GABAergic signaling, anticonvulsants, antidepressants, monoamine oxidase inhibitors, substance P (NK1) receptor antagonists, melanocortin receptor agonists and antagonists, lipase inhibitors, inhibitors of fat absorption, regulators of energy intake or metabolism, cannabinoid receptor modulators, agents for treating addiction, agents for treating metabolic syndrome, agents for treating hyperinsulinemia, agents for treating insulin resistance, agents for treating diabetes, peroxisome proliferator-activated receptor (PPAR) modulators; dipeptidyl peptidase 4 (DPP-4) antagonists, agents for treating cardiovascular disease, agents for treating elevated triglyceride levels, agents for treating low HDL, agents for treating hypercholesterolemia, and agents for treating hypertension.

In certain embodiments herein, the calorie restriction mimics as capsules or tablets are taken at least once per day.

At least one dosage form is desirably in the form of a sustained release formulation. Preferably, the sustained release formulation is provided in a manner that maintains a constant lowered level of cytosolic NADH for at least 12 h of a 24 h period.

These and other features of the present compositions and methods are set forth or become more fully apparent in the descriptions that follow and in the appended claims. The features and advantages may be realized and obtained by means of the formulations and combinations particularly pointed out in the appended claims. Furthermore, the features and advantages may be learned by the practice of the methods or are apparent from the description, as set forth hereinafter.

Embodiments herein provide compositions, methods of discovery and methods of use for the reduction of cytosolic levels of NADH in order to mimic life extension benefits of calorie restriction without restricting calorie intake. The compositions may contain specific compounds or agents extracted from plants as well as vitamins, minerals, antioxidants or other healthful nutrients. The compositions may contain natural extracts or agents derived therefore known to or determined to lower cytosolic levels of NADH together with other beneficial compounds known to the art. Such other compounds may comprise gums, fillers, preservatives and the like.

Screening and Identification of Calorie Restriction Mimics Based on NAD(P)H Autofluorescence in Yeasts Reduced forms of NAD(P)H show fluorescence with peaks of excitation and emission in the regions of 340 and 450 nm, respectively, that are used to monitor changes in cytosolic NAD(P)H levels. Because oxidized forms of these pyridine nucleotides have minimal fluorescence at this wavelength, a specific strain of Saccharomyces cerevisiae is used as the primary indicator and the assay is set up in a 98 well microtiter plate format. Fluorescence measurements are taken with an automated plate reader after 2 h of incubation in the presence of at least three log dilutions of the candidate calorie restriction mimic under investigation.

Four examples of substances known from the literature to lower cytosolic NADH levels were tested to validate the method.

EXAMPLE 1

Inhibition of Glycolysis by 2-deoxy-D-glucose

By replacing the glucose of the yeast culture medium with 2-deoxy-D-glucose (2DG), cytosolic NADH levels are reduced. 2DG may be specific for the hexokinase reaction. In the presence of glycolytic inhibitors, NADH or NAD(P)H concentrations are lowered consistent with the supposition that differences observed in total NADH reflect differences in available cytosolic levels necessary to mimic calorie restriction.

Oral or other administration of 2DG to a human similarly increases the $NAD^+$/NADH ratio and reduced the NADH or NAD(P)H concentrations.

EXAMPLE 2

The Stimulator of NADH-Quinone Oxidoreductase I (NQ01) β-Lapachone

By enhancing oxidation of cytosolic NADH through the stimulation of cytosolic NADH-quinone oxidoreductase 1 (NQ01), an effect accompanied by the activation of AMP-activated protein kinase, stimulation of mitochondrial biogenesis and increased energy expenditure, will be achieved. To stimulate NQ01, a natural substrate β-lapachone was employed at a concentration of 1 to 100 µM in the yeast system.

EXAMPLE 3

Direct Stimulation of Mitochondrial Consumption of Cytosolic NADH by Oxaloacetic Acid A documented approach to achieve lowering of cytosolic NADH is to accelerate its consumption by mitochondria. One such mitochondrial-acting calorie restriction mimic is oxaloacetic acid.

EXAMPLE 4

Stimulation of Plasma Membrane Redox System Utilization of Cytosolic NADH

The plasma membrane redox system is responsible for 10 to 50% of the oxidation of NADH in normal cells. By stimulating this activity, further reduction of cytosolic NADH levels, independent of mitochondrial utilization and of consumption by cytosolic NADH oxidoreductases will be achieved. Examples of potential stimulators of plasma membrane redox are melatonin or indoleamine.

TABLE 1

Concentration of known stimulators of NADH oxidation to increase NADH consumption by 50% in the yeast system.

| NADH oxidation stimulator | µM |
|---|---|
| Oxaloacetic acid | 20 |
| Indoleamine | 10 |
| β-Lapachrone | 40 |
| 2-Deoxyglucose | 2000 |

Preparation of Yeast Culture for the Autofluorescence Assay

A 10 mL culture of S. cerevisiae (wild type-BY4741, available from American Type Culture Collection, Manassas, Va., ATCC Number 201388) Genotype/ORF/Gene MATa his3delta1 leu2delta0 met15delta0 ura3delta0. The yeast cells are grown overnight in Yeast Extract Peptone Dextrose (YEPD) liquid medium at 30 C with shaking. $OD_{600}$ of the culture should be between 0.800 and 1.000 prior to assay usage. To remove unwanted autofluorescence, the medium components are removed by the following process.

Aliquots of the yeast culture are transferred to individual 1 mL micro-centrifuge tubes, and the yeast are pelleted in a bench-top centrifuge by spinning at 1000 RPM for 10 min. Excessive centrifugation speeds (over 1000 rpm) are not used because they could damage the yeast; and live yeast are required for the assay. The medium is decanted, and the yeast are resuspended in an equal volume of 1× phosphate buffered saline (137 mM NaCl, 2.7 mM KCl, 10 mM $Na_2HPO_4$, 1.76 mM $KH_2PO_4$, pH 7.4) and 7.5 mM glucose (PBSG). The concentration of yeast to amplify the autofluorescence can be achieved at this point by resuspending the yeast in a volume of 1×PBSG which is smaller than the original 1 mL of media. The 1×PBSG suspension in centrifuged for 10 min at 1000 rpm to re-pellet the yeast which, following decanting of the supernatant, are resuspended in a new aliquot of 1×PBSG. This preparation of yeast is used in the subsequent autofluorescence measurements at an optical density (bulk turbidity) at 600 nm between 0.8 and 1.0.

For fluorescence reading samples are added to a black 96 well cell culture plate. For this assay, plates do not require any pre-treatment or coating. A 100 μL aliquot of the yeast cell suspension is added to two wells per plate as a control for unmodulated yeast NADH autofluorescence. The same volume of yeast is added to experimental wells along with 54 of the compound or preparation (mimetic, etc.) which is being tested. As a negative control 1-2 wells of 1×PBSG should be included on each plate. A single well of each compound or preparation 5 μL+100 μL of 1×PBSG should be added to account for the fluorescence due to additive.

Experiments are conducted using a Fluoroskan II (Titer-Tek) fluorescent plate reader, which is controlled by Genesis software v 2.0 and used in accordance with the manufacturer' instructions. The first parameter to be set is how many wells are to be scanned on a given plate. This menu is accessed by clicking on the icon resembling a perforated rectangle on the top menu bar etc. After being prompted to save an individual plate layout, the layout is saved by giving the .plt file a name. After creating or selecting a preexisting plate file, the parameters of the assay are then entered. These parameters include a) type—whether the measurement is a single measurement or series of measurement over a given time (kinetic), b) excitation and emission wavelengths (for NADH autofluorescence the excitation wavelength is 340 nm and the emission wavelength is 450 nm.) c) interval at which measurements should be taken (every 20 seconds is sufficient) d) duration of each reading which is set at 5 sec per well, and e) the duration of the measurement which is set to 1 hr.

Once samples are added to wells and the setup and selection of parameters have been accomplished, the assay is commenced by clicking on the icon which depicts a small person running. The machine returns a screen showing the selected plates and protocol files. Once these are verified, the OK button is selected, and the machine automatically collects assay data. During collection, the computer screen displays a screen sub-divided into 96 individual boxes which display the progress of the assay over time. Right clicking on any individual box brings up a magnified graph of the assay progress for the individual well. Clicking the individual graph screen again returns the display to the 96 well monitoring mode. When the assay is completed the machine offers a series of prompts or a single prompt regarding the data.

Data files cannot be opened by conventional spreadsheet in their original nomenclature. This can be overcome by saving a copy of the file and changing the suffix to .txt. Upon changing this, the data can be accessed either as a simple text file or by importing the data into a spreadsheet. Using Excel the data are imported using the data prompt.

Once all data are imported, analysis is commenced. The two columns of yeast data are averaged to yield a single average column which displays the NADH auto-fluorescence of untreated yeast over time. The auto fluorescence for treated samples is attained by subtracting the fluorescence of the treatments alone from the absorbance of the yeast with their respective treatments. The treatments which are most successful in mimicking a calorie restricted diet produce a large depletion of NADH auto-fluorescence over time (e.g. a larger and more negative slope) on a plot of fluorescence (450 nm) versus time.

Preparation of Potato Skins

Fresh or frozen potato peels (skins) are microbially decontaminated by autoclaving at 250° F. for 20 min. The autoclaved peels are layered on a dehydrator tray and dehydrated overnight (Oster Dehydrater FPSTDH0101 or equivalent). The potato skins are finely ground using a Kitchen Aid Professional 5 Plus mixer with grinder attachment or equivalent (advantageously 0.05 to 0.075 mm particle size and passing through a No. 200 sieve).

Dried materials are prepared in a manner similar that described above, and tinctures or infusions are prepared using 100 ml liquid and 125 mg dried material. The tinctures or infusions are then used in the yeast autofluorescence assay as described above.

TABLE 2

Comparison of efficacy of red Irish potato skins, sweet potato skins and red bean hull infusions and tinctures in depletion of NADH levels in yeast*
Relative NADH depletion
Based on Fluorescence (0 to 120 min)**

| Source (dried) | Infusion | Tincture |
|---|---|---|
| Red Irish potato skins | 1312 | 1206*** |
| Sweet potato skins | 824 | 813 |
| Red bean hulls | 725 | 1220 |
| Kidney bean hulls | 392 | No data |

*125 mg/ml hot water (infusion) or 125 mg/ml (tincture) diluted to a final concentration of 1:200 in the yeast assay.
**A depletion of 500 fluorescence units represents a 15 to 20% reduction in NADH amount.
***Values for infusions and tinctures were not statistically significant Preparation of Nutritional Supplements The ground potato skins are combined with turmeric and magnesium malate in the appropriate ratios and mixed by tumbling for 5 min.

The organic acids in pureed apples or apple juice are precipitated by addition of magnesium salts, i.e. magnesium sulfate, and after settling overnight at 4° C., the precipitate is collected by low speed centrifugation or decantation of the supernatant, which now contains the bulk of the sugars. The precipitate is then washed several times by addition of 0.2 M Mg salts to remove residual sugars with the precipitate being collected by centrifugation or by settling in the cold and decantation of the supernatant. This material can be used in place of or in addition to malic acid or a pharmaceutically acceptable salt thereof. Leaf sources of oxaloacetic acid are dried and milled as for potato peels.

All references cited herein are hereby incorporated by reference in their entireties to the extent they are not inconsistent with the present disclosure.

What is claimed is:

1. A nutritional supplement composition comprising:
a) at least one of dried and milled Irish potato (*Solanum tuberosum*) skins, dehydrated hot water extracts of whole Irish potatoes, dehydrated Irish potato skins, skins of sweet potato (*Ipomea batas*) or hulls of pigmented bean (*Phaseolus vulgarus*) seeds;
b) at least one of turmeric or curcumin;
c) at least one of $Mg^{2+}$-malate or sodium malate; and
d) one selected from the group consisting of oxaloacetic acid, $Mg^{++}$-oxaloacetate or other pharmaceutically acceptable salts of oxaloacetic acid;
wherein at least one of the dried and milled Irish potato (*Solanum tuberosum*) skins, the dehydrated hot water extracts of whole Irish potatoes, the dehydrated potato skins, the skins of sweet potato (*Ipomea batas*), the hulls of pigmented bean (*Phaseolus vulgarus*) seeds, the turmeric, the curcumin, the $Mg^{2+}$-malate, the sodium malate, the oxaloacetic acid, the $Mg^{++}$-oxaloacetate or the other pharmaceutically acceptable salts of oxaloacetic acid is in an amount sufficient to reduce cytosolic NADH to levels that mimic calorie restriction.

2. The nutritional supplement composition of claim 1, wherein the composition comprises a mixture of 1 part turmeric, 1 part $Mg^{2+}$-malate and 98 parts dehydrated Irish potato skins.

3. The nutritional supplement composition of claim 2, wherein the potato skins are freeze dried.

4. The nutritional supplement composition of claim 1 wherein the ratio of turmeric and sodium malate to dehydrated potato skins is from 1:10 to 1:100 (weight/weight) and wherein the ratio of $Mg^{2+}$-malate to dehydrated potato skins is from 1:10 to 1:100 (weight/weight).

5. The nutritional supplement composition of claim 1, wherein the potato skins are skins of Irish potatoes (*Solanum tuberosum*).

6. The nutritional supplement composition of claim 1, wherein the composition further includes a pharmaceutically acceptable carrier.

7. The nutritional supplement composition of claim 1, wherein the composition is provided at an amount between 200 mg and 1200 mg in a capsule or a tablet.

8. The nutritional supplement composition of claim 1, wherein the composition is orally administered.

9. The nutritional supplement composition of claim 1, wherein said composition is in the form of a soft gel, capsule, tablet, pill, granule, powder, solution, suspension, snack bar, pharmaceutically acceptable emulsion, microemulsion, solution, suspension, syrup or elixir.

10. The nutritional supplement composition of claim 1, wherein said composition is administered at a frequency necessary to maintain required constant levels of reduced NADH to serve as a calorie restriction mimic.

11. The nutritional supplement composition of claim 1, wherein said composition is in the form of a sustained release granule.

12. The nutritional supplement composition of claim 1 further comprising sugar-free apple extracts or apple products.

13. A nutritional supplement composition comprising:
a) at least one of dried and milled Irish potato (*Solanum tuberosum*) skins, dehydrated hot water extracts of whole Irish potatoes, dehydrated Irish potato skins, skins of sweet potato (*Ipomea batas*) or hulls of pigmented bean (*Phaseolus vulgarus*) seeds;
b) at least one of turmeric or curcumin; and
c) at least one of oxaloacetic acid, coleus (*Coleus* spp.) leaves, strawberry (*Frageria* spp.) leaves, $Mg^{++}$-oxaloacetate, or other pharmaceutically acceptable salts of oxaloacetic acid; and
d) $Mg^{2+}$-malate or sodium malate;
wherein at least one of the dried and milled Irish potato (*Solanum tuberosum*) skins, the dehydrated hot water extracts of whole Irish potatoes, the dehydrated potato skins, the skins of sweet potato (*Ipomea batas*), the hulls of pigmented bean (*Phaseolus vulgarus*) seeds, the turmeric, the curcumin, the oxaloacetic acid, the coleus (*Coleus* spp.) leaves, the strawberry (*Frageria* spp.) leaves, the $Mg^{++}$-oxaloacetate, or the other pharmaceutically acceptable salts of oxaloacetic acid is in an amount sufficient to reduce cytosolic NADH to levels that mimic calorie restriction.

14. The nutritional supplement composition of claim 13, wherein the composition is provided at an amount between 200 mg and 1200 mg in a capsule or a tablet.

15. The nutritional supplement composition of claim 13 further comprising sugar-free apple extracts or apple products.

16. A nutritional supplement composition comprising:
a) dehydrated Irish potato skins;
b) turmeric;
c) $Mg^{2+}$-malate; and
d) oxaloacetic acid;
wherein at least one of the dehydrated Irish potato skins, turmeric, $Mg^{2+}$-malate, or oxaloacetic acid is in an amount sufficient to reduce cytosolic NADH to levels that mimic calorie restriction.

* * * * *